(12) United States Patent
Carroll et al.

(10) Patent No.: US 8,048,895 B2
(45) Date of Patent: Nov. 1, 2011

(54) KAPPA OPIOID RECEPTOR LIGANDS

(75) Inventors: Frank Ivy Carroll, Durham, NC (US); Hernan A. Navarro, Chapel Hill, NC (US); James B. Thomas, Efland, NC (US); Tingwei Cai, High Point, NC (US)

(73) Assignee: Research Triangle Institute, Research Triangle Park, NC (US)

( * ) Notice: Subject to any disclaimer, the term of this patent is extended or adjusted under 35 U.S.C. 154(b) by 508 days.

(21) Appl. No.: 12/105,814

(22) Filed: Apr. 18, 2008

(65) Prior Publication Data

US 2009/0264462 A1 Oct. 22, 2009

(51) Int. Cl.
*A61K 31/445* (2006.01)
*C07D 251/00* (2006.01)
*C07D 401/00* (2006.01)
*C07D 271/00* (2006.01)
*C07D 487/00* (2006.01)

(52) U.S. Cl. ........ 514/317; 514/241; 514/256; 514/291; 514/292; 514/293; 546/81; 546/82; 546/84; 546/139; 546/152; 540/577

(58) Field of Classification Search .................. 514/307, 514/252, 317, 241, 256, 291, 293; 546/146, 546/81, 82, 84, 139, 152; 540/577
See application file for complete search history.

(56) References Cited

U.S. PATENT DOCUMENTS

| | | | |
|---|---|---|---|
| 5,128,118 A | 7/1992 | Carroll et al. | |
| 5,141,959 A | 8/1992 | Carroll et al. | |
| 5,298,499 A | 3/1994 | Carroll et al. | |
| 5,380,848 A | 1/1995 | Kuhar et al. | |
| 5,411,965 A * | 5/1995 | Reid et al. ................ | 514/279 |
| 5,413,779 A | 5/1995 | Kuhar et al. | |
| 5,496,953 A | 3/1996 | Kuhar et al. | |
| 5,736,123 A | 4/1998 | Carroll | |
| 5,831,095 A | 11/1998 | Gonzalez et al. | |
| 5,935,953 A | 8/1999 | Kuhar et al. | |
| 6,123,917 A | 9/2000 | Carroll | |
| 6,329,520 B1 | 12/2001 | Carroll et al. | |
| 6,358,492 B1 | 3/2002 | Kuhar et al. | |
| 6,416,735 B1 | 7/2002 | Carroll et al. | |
| 6,479,509 B1 | 11/2002 | Carroll | |
| 6,531,481 B2 | 3/2003 | Carroll et al. | |
| 6,531,483 B1 | 3/2003 | Kuhar et al. | |
| 6,538,010 B1 | 3/2003 | Carroll | |
| 6,552,032 B2 | 4/2003 | Carroll et al. | |
| 6,559,159 B2 | 5/2003 | Carroll et al. | |
| 6,593,348 B2 | 7/2003 | Carroll et al. | |
| 6,706,880 B2 | 3/2004 | Carroll et al. | |
| 6,900,228 B1 | 5/2005 | Carroll et al. | |
| 6,974,824 B2 | 12/2005 | Carroll et al. | |
| 7,011,813 B2 | 3/2006 | Kuhar et al. | |
| 7,189,737 B2 | 3/2007 | Kuhar et al. | |
| 7,291,737 B2 | 11/2007 | Kuhar et al. | |
| 2002/0132828 A1 | 9/2002 | Carroll et al. | |
| 2003/0158415 A1 | 8/2003 | Carroll et al. | |
| 2003/0176434 A1 | 9/2003 | Carroll | |
| 2004/0146518 A1 | 7/2004 | Carroll et al. | |
| 2006/0069111 A1 | 3/2006 | Carroll | |
| 2006/0183743 A1 | 8/2006 | Frank et al. | |
| 2006/0241135 A1 | 10/2006 | Carroll et al. | |
| 2007/0027182 A1 | 2/2007 | Carroll et al. | |
| 2009/0264462 A1 | 10/2009 | Carroll et al. | |

FOREIGN PATENT DOCUMENTS

WO  WO 02/053533 A2  7/2002

OTHER PUBLICATIONS

U.S. Appl. No. 12/551,072, filed Aug. 31, 2009, Carroll.
P. Portoghese, "The Design of δ-Selective Opioid Receptor Antagonists", IL Fannaco, 1993, vol. 48, No. 2, pp. 243-251.
P. Portoghese et al., "Binaltorphimine and Nor-Binaltorphimine, Potent and Selective κ-Opioid Receptor Antagonists", Life Sciences, 1987, vol. 40, No. 13, pp. 1287-1292.
S. Olmsted, et al., "A Remarkable Change of Opioid Receptor Selectivity on the Attachment of a Peptidomimetic κ Address Element to the δ Antagonist, Natrindole: 5'-[ ($N^2$-Alkylamidino)methyl]naltrindole Derivatives as a Novel Class of κ Opioid Receptor Antagonists", J. Med. Chem., 1993, vol. 36, No. 1, pp. 179-180.
R. Jones, et al., "Mutational Evidence for a Common κ Antagonist Binding Pocket in the Wild-Type κ and Mutant μ[K303E] Opioid Receptors†", The Journal of Medical Chemistry, vol. 41, No. 25, Dec. 3, 1998, pp. 4911-4914.
R. Schwyzer, "ACTH: A Short Introductory Review", Ann. N. Y. Acad. Sci., 1977, vol. 247, pp. 3-26.
K. Trujillo, et al., Changes in Prodynorphin Peptide Content Following Treatment with Morphine or Amphetamine: Possible Role in Mechanisms of Action of Drug of Abuse:, NIDA Res. Monogr., 1989, vol. 95, pp. 550-551.
P. Smiley, et al., "Effects of Cocaine on Extrapyramidal and Limbic dynorphin systems[1]", J. Pharmacol. Exp. Ther.,vol. 253, No. 3, 1990, pp. 938-943.
A. Corbett, et al., "$Dynorphin_{1-8}$ and $Dynorphin_{1-9}$ are Ligands for the κ-Subtype of Opiate Receptor", Nature, vol. 299, No. 5878, 1982, pp. 79-81.
R. Spangle, et al., "Opposing Tonically Active Endogenous Opioid Systems Modulate the Mesolimbic Dopaminergic Pathway", Proc. Natl. Acad. Sci. USA, vol. 89, 1992, pp. 2046-2050.
R. Spangle, et al., "Modulation of Morphine-Induced Sensitization by Endogenous κ-Opioid systems in the rat", Neurosci. Lett., vol. 153, 1993, pp. 232-236.
J. Zadina et al., "A Potent and Selective Endogenous Agonist for The μOpiate Receptor", Nature, vol. 386, 1997, pp. 499-502.
D. Zimmerman, et al., "New Structural Concepts for Narcotic Antagonists Defined in A 4-Phenylpiperidine Series", Nature, vol. 275, 1978, pp. 332-334.
D. Zimmerman, et al., "Further Investigation of Novel 3-methyl-4-phenylpiperidine Narcotic Antagonists", In Proceedings of the 40th Annual Scientific Meeting of the Committee on Problems of Drug Dependence, 1978, pp. 237-247.

(Continued)

*Primary Examiner* — Sreeni Padmanabhan
*Assistant Examiner* — Sahar Javanmard
(74) *Attorney, Agent, or Firm* — Oblon, Spivak, McClelland, Maier & Neustadt, L.L.P.

(57) ABSTRACT

Kappa opioid receptor antagonists are provided that yield significant improvements in functional binding assays to kappa opioid receptors, and the use of these antagonists in treatment of disease states that are ameliorated by binding of the kappa opioid receptor such as heroin or cocaine addictions.

32 Claims, 3 Drawing Sheets

OTHER PUBLICATIONS

D. Zimmerman, et al., "Structural Requirements for Affinity and Intrinsic Activity At The Opiate Receptor Defined in 4-Phenylpiperidine and Related Series", In Problems of Drug Dependence, 1981, Proceedings of the 43$^{rd}$ Annual Scientific Meeting, The committee on Problems of Drug-Dependence, Inc., NIDA Research Monograph., vol. 41, 1982, pp. 112-118.

D. Zimmerman, et al., "Synthesis and Analgesic Properties of N-Substituted trans-4a-Aryldecahydroisoquinolines", J. Med. Chem., vol. 31, 1988, pp. 555-560.

D. Zimmerman, et al., "Structure-Activity Relationships of trans-3,4-Dimethyl-4-(3-hydroxyphenyl)piperidine Antagonists for µ- and κ-Opioid Receptors", J. Med. Chem., vol. 36, No. 20, 1993, pp. 2833-2841.

D. Zimmerman, et al., "Opioid Receptor Antagonists: Comparison of trans-3-,4-dimethyl-4-phenylpiperidines and Their Use In The Development of A Model Of Opioid Receptors", Pharmacol. Rev. in Press.

U.S. Appl. No. 08/506,541, file Jul. 24, 1995, Kuhar, et al.
U.S. Appl. No. 08/701,503, file Aug. 22, 1996, Carroll, et al.
U.S. Appl. No. 60/107,902, file Nov. 10, 1998, Carroll, et al.
U.S. Appl. No. 09/537,668, file Mar. 29, 2000, Carroll, et al.
U.S. Appl. No. 10/259,780, filed Sep. 30, 2002, Carroll, et al.
U.S. Appl. No. 11/863,587, file Sep. 28, 2007, Kuhar, et al.
U.S. Appl. No. 12/911,244, filed Oct. 25, 2010, Carroll, et al.

J. Aldrich, "Analgesics", In Burger's Medicinal Chemistry and Drug Discovery, Wolff, M.E. Eds.; John Wiley & sons: New York, 1996, vol. 3.

J. Volpicelli, et al., "Naltrexone in the Treatment of Alcohol Dependence", Arch. Gen. Psychiatry, 1992, vol. 49, pp. 876-880.

J. Volpicelli, et al. "Effect of Naltrexone on Alcohol "high" in Alcoholics", Am. J. Psychiatry, 1995, vol. 152, pp. 613-615.

A. Marki, et al., "µ-Opioid Receptor Specific Antagonist Cyprodime: Characterization by In Vitro Radioligand and [$^{35}$S]GTPγS Binding Assays", Eur. J. Pharmacol, 1999, vol. 383, No. 2, pp. 209-214.

J. Thomas, et al., "Investigation of the N-Substituent Conformation Governing Potency and µ Receptor Subtype-Selectivity in (+)-(3$R$,4$R$)-Dimethyl-4-(3-hydroxyphenyl)-piperidine Opioid Antagonists", J. Med. Chem., vol. 41, No. 11, 1998, pp. 1980-1990.

J. Thomas, et al., "Identification of an Opioid K Receptor Subtype-Selective N-Substituent for (+)-(3$R$,4$R$)-Dimethyl-4-(3-hydroxyphenyl)piperidine", J. Med. Chem., vol. 41, No. 26, 1998, pp. 5188-5197.

J. Werner, et al., "Synthesis of *trans*-3,4-Dimethyl-4-(3-hydroxyphenyl)piperidine Opioid Antagonists: Application of the *Cis*-Thermal Elimination of Carbonates to Alkaloid Synthesis", J. Org. Chem., vol. 61, 1996, pp. 587-597.

\* cited by examiner

1, $R_1 = R_2 = H$
2, $R_1 = R_2 = COCH_3$ 3    4    5

6    7    8

9a; R = $CH_3$
9b; R = $CH_2C_3H_5$ 10    11    12

13    14    15

KAPPA OPIOID RECEPTOR LIGANDS

BACKGROUND OF THE INVENTION

1. Field of Invention

The present invention relates to compounds that bind with high affinity and/or specificity to kappa opioid receptors.

2. Discussion of the Background

The study of compounds exerting their actions via the opioid receptor system has continued for nearly eight decades. Though this has been a broad effort, the fundamental driving force for this endeavor relates to the elimination or reduction of the side-effect profile produced by the most frequently used or abused opiates morphine (1) and heroin (2) in FIG. 1. Among the many side effects produced by compounds 1 and 2, addiction, tolerance and respiratory depression are of greatest concern when heroin abuse is considered. Though its use waned in the late 70s, increases in both the purity and availability of this drug have promoted a serious resurgence of illegal use. In the study and treatment of substance abuse, antagonists for the opioid receptors such as naltrexone (3) (FIG. 1) have played a prominent role. In recent years, researchers studying the physiological mechanisms underlying addiction have sought antagonists selective for each of the three opioid receptor subtypes mu, delta and kappa. Extensive research efforts along these lines lead to the discovery of several such compounds with examples including cyprodime (mu, 4), naltrindole (delta, 5) and nor-binaltorphimine (kappa, 6) (FIG. 1). Of the three, the kappa receptor has only begrudgingly yielded antagonists and, of the known examples, all stem from modification of the prototype, nor-binaltorphimine (nor-BNI, 6).

Portoghese in his pioneering work provided not only the second and third generation kappa antagonists 5'-[(N2-butylamidino)methyl]naltrindole (7) and C5'-guanidinylnaltrindole (GNTI, 8) but also convincing evidence that the Glu297 residue in transmembrane helix 6 of the kappa receptor is the principle address site influencing the kappa selectivity found in 6-8 (FIG. 1). In terms of the message address concept as applied by Portoghese to opioid small-molecules, it is the pendant amine functionality (noted by asterisks in the chart) that functions as the kappa address element for compounds 6-8 by interacting with the Glu297 residue which is present in the kappa but not in the mu receptor.

In terms of substance abuse treatment, antagonists selective for the kappa receptor have been the least studied primarily due to the limited bio-availability of 6 and its analogs. However, mounting evidence that the endogenous kappa opioid system opposes the actions of mu agonists like 2 suggests that antagonists selective for the kappa receptor system could suppress or eliminate the symptoms of withdrawal which arise from an overactive kappa receptor system and thus could promote abstinence and prevent relapse. Therefore, the development of novel kappa antagonists possessing improved pharmacokinetic profiles would be of great value.

As is obvious from the examples above, the morphinan substructure of 3 has served as the preeminent template upon which selective antagonists have been constructed. Contrary to these efforts, our work in this field started from the relatively unstudied N-substituted trans-(3,4)-dimethyl-4-(3-hydroxyphenyl)piperidine class of opioid antagonist discovered by Zimmerman et al. Compounds like 9a and 9b (FIG. 1) were novel opioid antagonists because their intrinsic antagonist activity was not mediated by the structure of their N-substituent (i.e. the N-methyl (9a) and N-cyclopropylmethyl (9b) analogs in the phenylpiperidine series are both pure antagonists). Indeed, no N-substituent has been discovered which converts this series of compound into an agonist. Compounds 10-12 (FIG. 1) represent some of the structures tried to date. In this connection we recently demonstrated that compounds bearing the trans-cinnamyl N-substituent, as found in 13 (FIG. 1), most closely reproduced the potency at the mu opioid receptor of the flexible N-substituted analogs (10-12). In fact, the comparable mu receptor potencies demonstrated by analogs trans-(3,4)-dimethyl-4-(3-hydroxyphenyl)piperidine possessing the trans-cinnamyl moiety lead us to speculate that in their biologically active conformation, compounds such as 10-12 have the connecting chain and appended ring in their N-substituent extended away from the piperidine nitrogen in a manner consistent with the trans-cinnamyl skeleton like that found in 13.

In our more recent studies comparing opioid receptor potency and selectivity to N-substituent changes in this series of antagonists, we discovered 14-18, where Q is NH, $CH_2$, O, S, SO, or $SO_2$ (FIG. 1). These compounds were obtained from the screening of libraries of compounds which were biased for opioid antagonist activity by incorporation of trans-(3,4)-dimethyl-4-(3-hydroxyphenyl)piperidine into each ligand. In biological testing those compounds (14-18) were found to possess kappa opioid receptor subtype selectivity in functional binding assays. Our earlier work in this class of compounds is described in, for example, U.S. patent publication Nos. 2002/0132828 and 2006/0183743. The present application is directed to this new group of compounds.

SUMMARY OF THE INVENTION

It is an object of the invention to provide compounds which bind to kappa opioid receptors with high affinity.

It is another object of the invention to provide compounds which bind to kappa opioid receptors with high specificity.

It is another object of the invention to provide compounds which bind to kappa opioid receptors with high affinity and specificity in functional assays.

The objects of the present invention, and others, are accomplished with the compounds, compositions and methods described above which have the above advantages.

BRIEF DESCRIPTION OF THE FIGURES

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE INVENTION

Figure 1A:
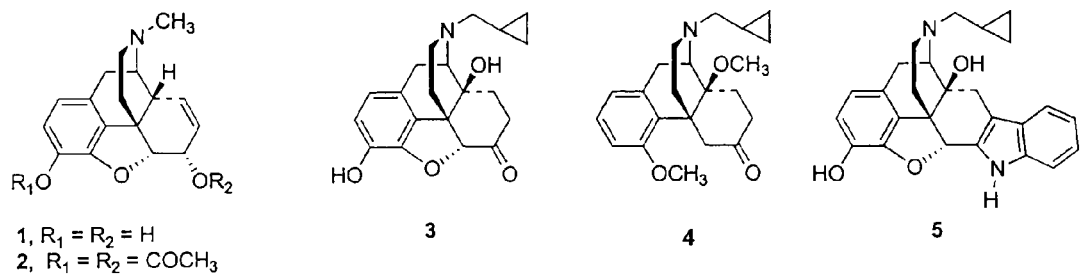
FIG. 1: chemical structure of compounds (1)-(18)
Figure 1A:
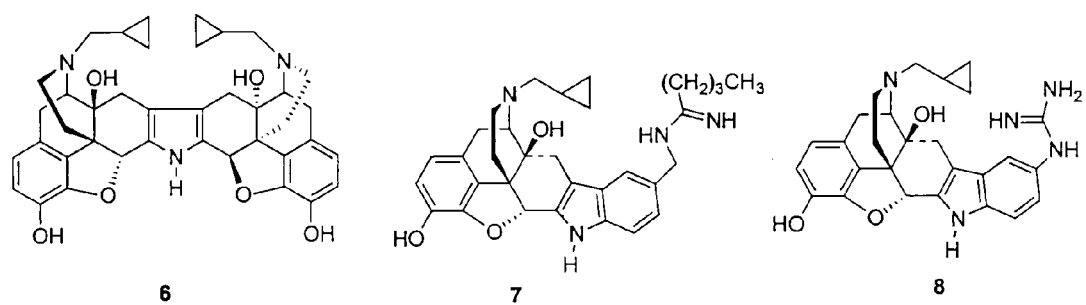
Figure 1A:
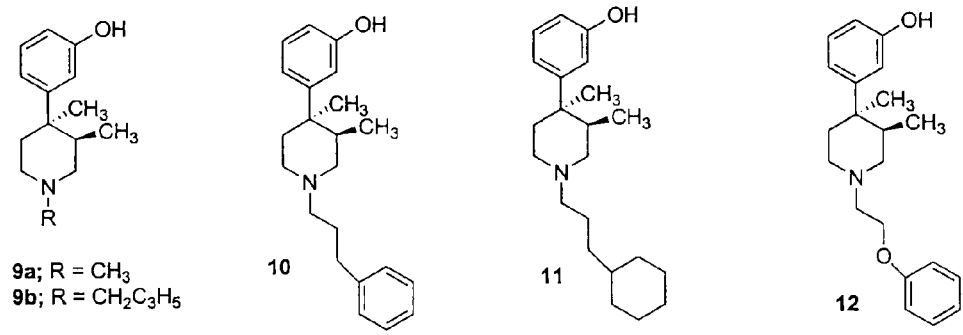
Figure 1A:
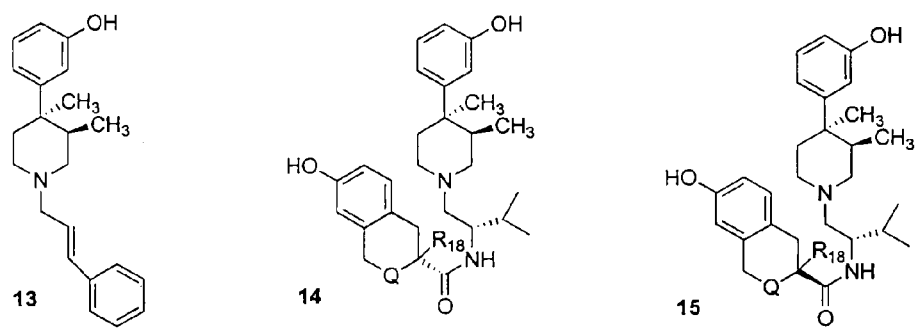
Figure 1B:
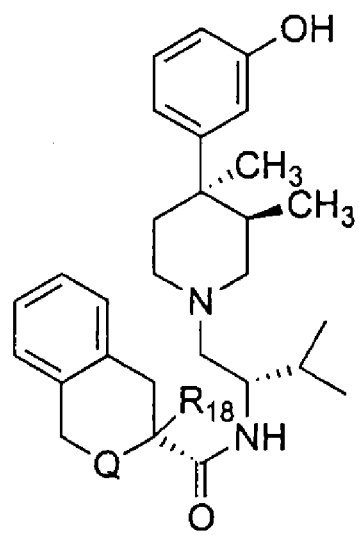
Figure 1B:
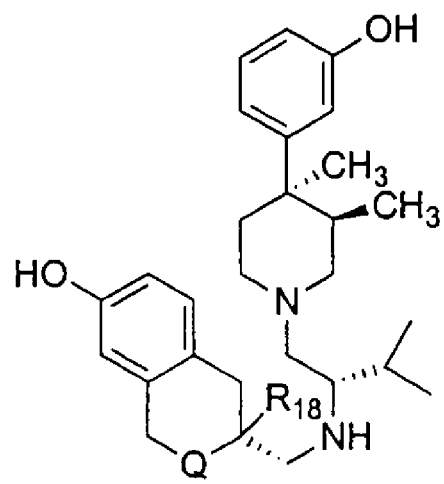
Figure 1B:
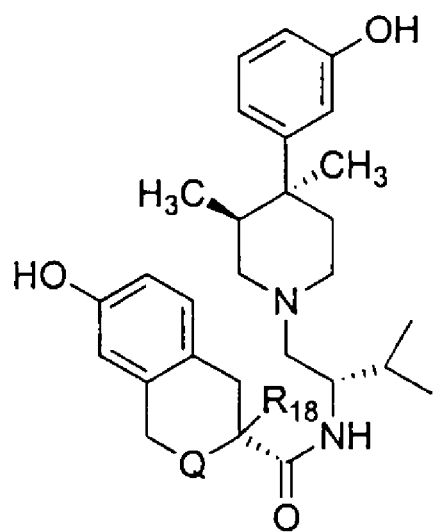

The present invention provides kappa opioid antagonists that bind to kappa opioid receptors with high affinity and/or specificity. Compounds of the present invention are those represented by the formula (I):

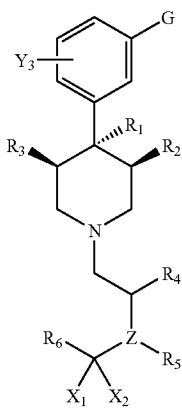
(I)

where

G is H, OH, $OC_{1-6}$ alkyl, $OCOC_{1-8}$ alkyl, $CONH_2$, NHCHO, $NH_2$, $NHSO_2C_{1-8}$ alkyl, or $NHCO_2C_{1-8}$ alkyl;

$R_1$ is $C_{1-8}$ alkyl, or one of the following structures:

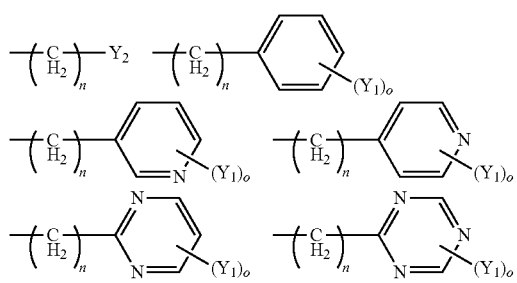

each $Y_1$ is, independently, H, Br, Cl, F, CN, $CF_3$, $NO_2$, $N_3$, $OR_8$, $CO_2R_9$, $C_{1-6}$ alkyl, $NR_{10}R_{11}$, $NHCOR_{12}$, $NHCO_2R_{12}$, $CONR_{13}R_{14}$, or $CH_2(CH_2)_nY_2$, or two adjacent $Y_1$ groups form a —O—$CH_2$—O— or —O—$CH_2CH_2$—O— group;

each $Y_2$ is, independently, H, $CF_3$, $CO_2R_9$, $C_{1-6}$alkyl, $NR_{10}R_{11}$, $NHCOR_{12}$, $NHCO_2R_{12}$, $CONR_{13}R_{14}$, $CH_2OH$, $CH_2OR_8$, or $COCH_2R_9$;

$Y_3$ is H, Br, Cl, F, CN, $CF_3$, $NO_2$, $N_3$, $OR_8$, $CO_2R_9$, $C_{1-6}$ alkyl, $NR_{10}R_{11}$, $NHCOR_{12}$, $NHCO_2R_{12}$, $CONR_{13}R_{14}$, or $CH_2(CH_2)_nY_2$;

$R_2$ is H, $C_{1-8}$ alkyl, $C_{3-8}$ alkenyl, $C_{3-8}$ alkynyl or $CH_2$-aryl substituted by one or more groups $Y_1$;

$R_3$ is H, $C_{1-8}$ alkyl, $C_{3-8}$ alkenyl, $C_{3-8}$ alkynyl or $CH_2$-aryl substituted by one or more groups $Y_1$;

wherein $R_2$ and $R_3$ may be bonded together to form a $C_{2-8}$ alkyl group;

$R_4$ is hydrogen, $C_{1-8}$ alkyl, $CO_2C_{1-8}$ alkylaryl substituted by one or more groups $Y_1$, $CH_2$-aryl substituted by one or more groups $Y_1$ or $CO_2C_{1-8}$ alkyl;

Z is N, O or S, wherein when Z is O or S, there is no $R_5$;

$R_5$ is H, $C_{1-8}$ alkyl, $C_{3-8}$ alkenyl, $C_{3-8}$ alkynyl, $CH_2CO_2C_{1-8}$ alkyl, $CO_2C_{1-8}$ alkyl or $CH_2$-aryl substituted by one or more groups $Y_1$;

n is 0, 1, 2 or 3;

o is 0, 1, 2, or 3;

$R_6$ is a group selected from the group consisting of structures (a)-(p):

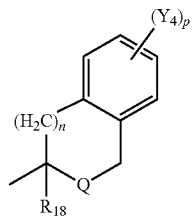
(a)

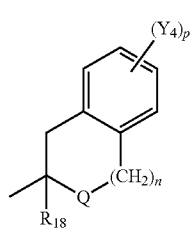
(b)

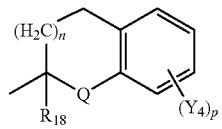
(c)

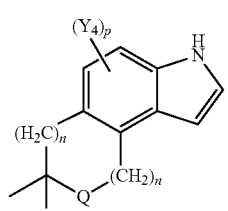
(d)

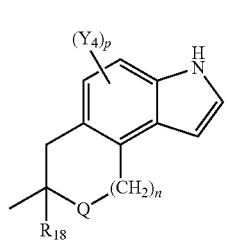
(e)

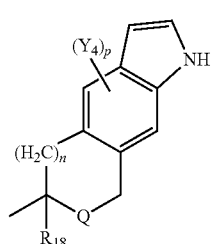
(f)

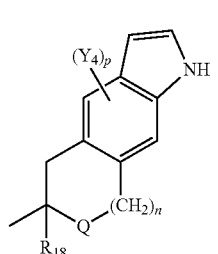
(g)

(h) 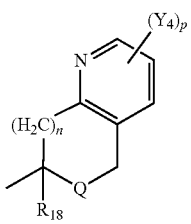

(i) 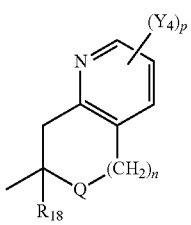

(j) 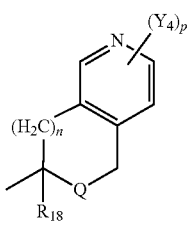

(k) 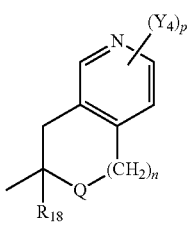

(l) 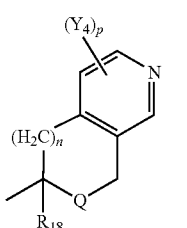

(m) 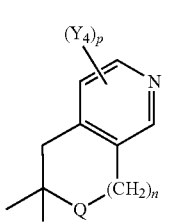

(n) 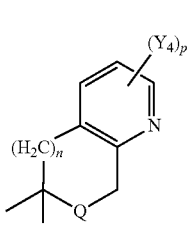

(o)

(p)

Q is $NR_7$, $CH_2$, O, S, SO, or $SO_2$;

each $Y_4$ is, independently, H, Br, Cl, F, CN, $CF_3$, $NO_2$, $N_3$, $OR_8$, $CO_2R_9$, $C_{1-6}$ alkyl, $NR_{10}R_{11}$, $NHCOR_{12}$, $NHCO_2R_{12}$, $CONR_{13}R_{14}$, or $CH_2(CH_2)_nY_2$, or two adjacent $Y_4$ groups form a —O—$CH_2$—O— or —O—$CH_2CH_2$—O— group;

p is 0, 1, 2, or 3;

$Y_5$ is H, Br, Cl, F, CN, $CF_3$, $NO_2$, $N_3$, $OR_8$, $CO_2R_9$, $C_{1-6}$ alkyl, $NR_{10}R_{11}$, $NHCOR_{12}$, $NHCO_2R_{12}$, $CONR_{13}R_{14}$, or $CH_2(CH_2)_nY_2$;

$X_1$ is hydrogen, $C_{1-8}$ alkyl, $C_{3-8}$alkenyl, or $C_{3-8}$alkynyl;

$X_2$ is hydrogen, $C_{1-8}$alkyl, $C_{3-8}$alkenyl, or $C_{3-8}$alkynyl;

or $X_1$ and $X_2$ together form =O, =S, or =NH;

$R_7$ is H, $C_{1-8}$ alkyl, $CH_2$-aryl substituted by one or more substituents $Y_1$, $NR_{10}R_{11}$, $NHCOR_{12}$, $NHCO_2R_{13}$, $CONR_{14}R_{15}$, $CH_2(CH_2)_nY_2$, or C(=NH)$NR_{16}R_{17}$;

each of $R_8$, $R_9$, $R_{10}$, $R_{11}$, $R_{12}$, $R_{13}$, $R_{14}$, $R_{15}$, $R_{16}$ and $R_{17}$ is, independently, H, $C_{1-8}$ alkyl, $CH_2$-aryl substituted by one or more substituents H, OH, Br, Cl, F, CN, $CF_3$, $NO_2$, $N_3$, $C_{1-6}$ alkyl, or $CH_2(CH_2)_nY_2'$;

$Y_2'$ is H, $CF_3$, or $C_{1-6}$ alkyl;

$R_{18}$ is $C_{1-8}$ alkyl, $C_{2-8}$ alkenyl, $C_{3-8}$ alkenyl, $CH_2OR_5$, or $CH_2$-aryl substituted by one or more substituents $Y_1$;

or a pharmaceutically acceptable salt thereof.

Preferably, the compounds of the present invention are those represented by the formula I as shown above, wherein G, $R_1$, $R_4$, $R_5$, $Y_1$, $Y_2$, Z, n, $X_1$, $X_2$, Q and $R_7$-$R_{17}$ are as indicated above;

$Y_3$ is H;

$R_2$ and $R_3$ are each, independently, H, $C_{1-8}$ alkyl, $C_{3-8}$ alkenyl, $C_{3-8}$ alkynyl, or $CH_2$-aryl substituted by one or more substituents $Y_1$; and $R_6$ is a group having a formula selected from the group consisting of structures (a)-(p) above.

More preferably, the compounds of the present invention are those represented by the formula I as shown above, wherein G, $Y_1$, $Y_2$, $R_4$, $R_5$, Z, n, $X_1$, $X_2$, Q and $R_8$-$R_{15}$ are as indicated above;

$R_1$ is $C_{1-8}$ alkyl, or one of the following structures

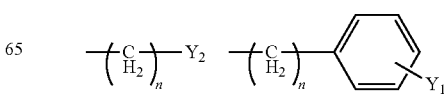

$Y_3$ is H;

$R_2$ and $R_3$ are each, independently, H or $C_{1-8}$ alkyl, wherein $R_2$ and $R_3$ cannot both be H at the same time;

$R_6$ is a formula selected from the structures (a)-(p) shown above; and $R_7$ is H, $C_{1-8}$ alkyl, $CH_2$aryl substituted by one or more substituents $Y_1$, $NR_{10}R_{11}$, $NHCOR_{12}$, $NHCO_2R_{13}$, $CONR_{14}R_{15}$, or $CH_2(CH_2)_nY_2$.

Still more preferably, the compound of the present invention are those represented by the formula I as shown above, wherein G, $Y_1$, Z, n, $X_1$, $X_2$, Q and $R_8$-$R_{15}$ are as noted above;

$R_1$ is $C_{1-8}$ alkyl;

$Y_2$ is H, $CF_3$, $CO_2R_9$, $C_{1-6}$ alkyl, $NR_{10}R_{11}$, $NHCOR_{12}$, $NHCO_2R_{12}$, $CONR_{13}R_{14}$, $CH_2OH$, $CH_2OR_8$, or $COCH_2R_9$;

$Y_3$ is H;

$R_2$ and $R_3$ are each, independently, H or methyl, wherein $R_2$ and $R_3$ cannot both be H at the same time;

$R_4$ is H, $C_{1-8}$ alkyl, $CO_2C_{1-8}$alkyl, or aryl substituted by one or more substituents $Y_1$ and the stereocenter adjacent to $R_4$ is in an (S) configuration;

$R_5$ is H, $C_{1-8}$ alkyl, or $CH_2CO_2C_{1-8}$ alkyl;

$R_6$ is a group having a formula selected from the group consisting of structures (a)-(c) and (h)-(p); and $R_7$ is H, $C_{1-8}$ alkyl, $CH_2$aryl substituted by one or more substituents $Y_1$, $NR_{10}R_{11}$, $NHCOR_{12}$, $NHCO_2R_{13}$, $CONR_{14}R_{15}$, or $CH_2(CH_2)_nY_2$.

Most preferably, the compounds of the present invention are those represented by the formula I as shown above, wherein G, $Y_1$, Z, n, $X_1$, $X_2$, Q and $R_8$-$R_{14}$ are as indicated above;

$R_1$ is methyl, $Y_2$ is H, $CF_3$, $CO_2R_9$, $C_{1-6}$ alkyl, $NR_{10}R_{11}$, $NHCOR_{12}$, $NHCO_2R_{12}$, $CONR_{13}R_{14}$, $CH_2OH$, $CH_2OR_8$, or $COCH_2R_9$;

$Y_3$ is H;

$R_2$ and $R_3$ are each H or methyl, such that when $R_2$ is H, $R_3$ is methyl and vice versa;

$R_4$ is $C_{1-8}$ alkyl, or $CO_2C_{1-8}$ alkyl, and the stereocenter adjacent to $R_4$ has a configuration of (S);

$R_5$ is H;

$R_6$ is a group having a formula selected from the group consisting of structures (a) and (b); and $R_7$ is H, $C_{1-8}$ alkyl, $CH_2$aryl substituted by one or more substituents $Y_1$ or $CH_2(CH_2)_nY_2$.

A most preferred set of compounds are the compounds of formula 14-18 as shown in FIG. 1, where Q is NH, $CH_2$, O, S, SO, or $SO_2$ and $R_{18}$ is as defined above.

A particularly preferred $OR_8$ is OH, i.e., $R_8$ is hydrogen.

As used throughout this disclosure, the terms "alkyl group" or "alkyl radical" encompass all structural isomers thereof, such as linear, branched and cyclic alkyl groups and moieties. Unless stated otherwise, all alkyl groups described herein may have 1 to 8 carbon atoms, inclusive of all specific values and subranges therebetween, such as 2, 3, 4, 5, 6, or 7 carbon atoms.

The alkenyl group or alkynyl group may have one or more double or triple bonds, respectively. As will be readily appreciated, when an alkenyl or alkynyl group is bonded to a heteroatom a double or triple bond is not formed with the carbon atom bonded directly to the heteroatom. Unless stated otherwise, all alkenyl and alkynyl groups described herein may have 3 to 8 carbon atoms, inclusive of all specific values and subranges therebetween, such as 4, 5, 6, or 7 carbon atoms.

The aryl group is a hydrocarbon aryl group, such as a phenyl, naphthyl, phenanthryl, anthracenyl group, which may have one or more $C_{1-4}$ alkyl group substituents.

The compounds of the present invention are opiates which are preferably antagonists that are selective for the kappa receptor. The κ/μ selectivity may be at least 2:1, but is preferably higher, e.g., at least 5:1, 10:1, 20:1, 25:1, 50:1, 100:1, 200:1 or even 500:1. The κ/δ selectivity may be at least 2:1, but is preferably higher, e.g., at least 5:1, 10:1, 20:1, 25:1, 50:1, 100:1, 200:1, 250:1, 500:1, 1000:1, 10,000:1, 15,000:1, 20,000:1, 25,000:1 or even 30,000:1. These ranges include all specific ranges and subranges therebetween as well as all combinations of κ/μ and κ/δ selectivity.

Figure 2:
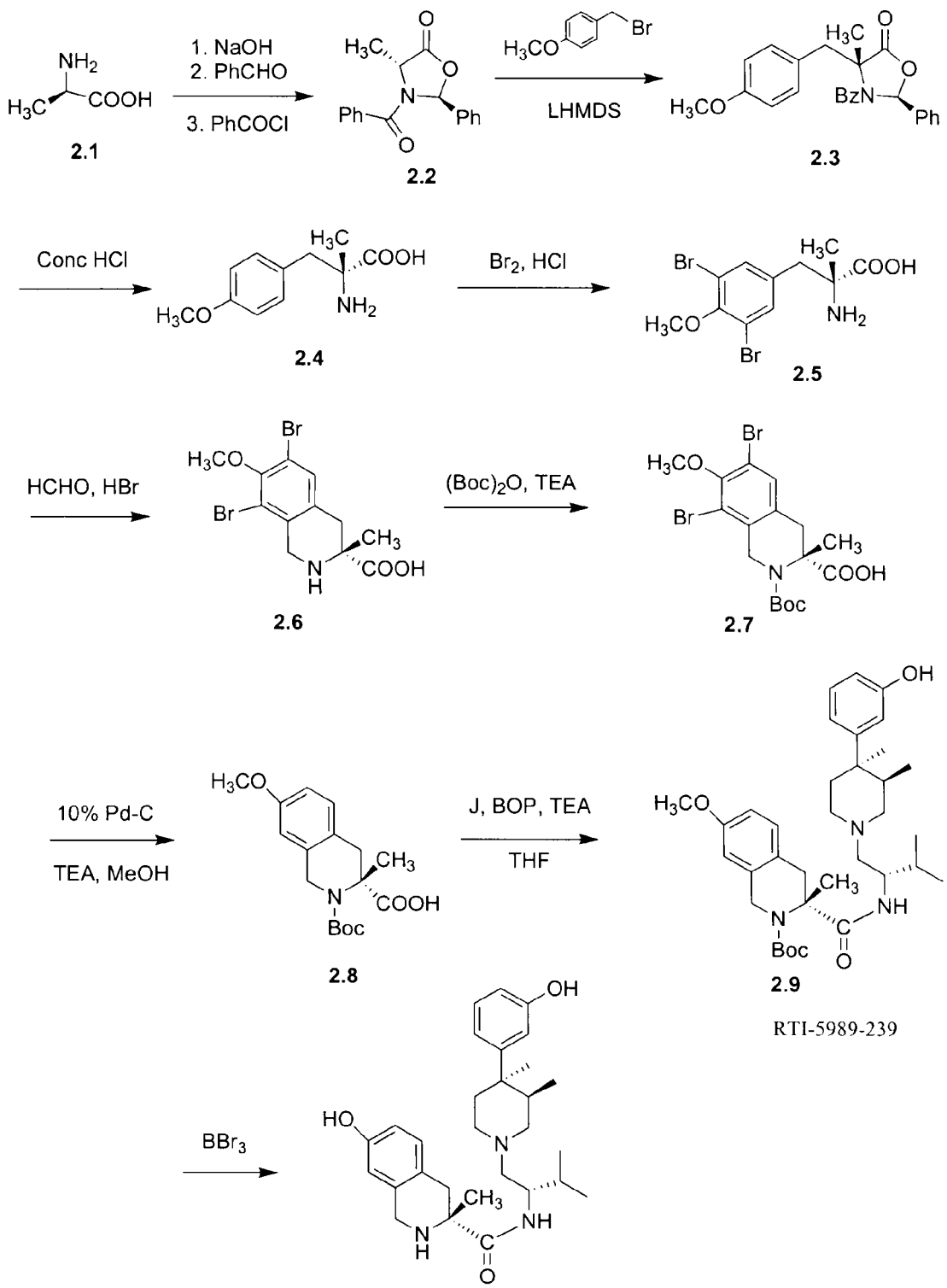
FIG. 2: examples of synthetic routes to compounds RTI-5989-239 and RTI-5989-240.

The compound 14, Q=NH and $R_{18}$=$CH_3$ of the present invention may be synthesized, for example, in accordance with the reaction sequence shown in FIG. 2. The synthesis of RT15989-240 (14, Q=NH and $R_{18}$=$CH_3$) is convergent with one of the key starting materials being tetrahydroisoquinoline derivative 2.8. Preparation of this key intermediate started from D-alanine (2.1) by first making the sodium salt of D-alanine using sodium hydroxide in ethanol. This salt was then converted to chiral oxazolidinone 2.2 by condensation with benzaldehyde under azeotropic distillation conditions followed by benzoylation using benzoyl chloride. Stereoselective alkylation of 2.2 with 4-methoxybenzyl bromide and lithium hexamethyldisilazide at −78° C. gave the benzylated intermediate 2.3 with retention of configuration of its asymmetric center. Formation of the tetrahydroisoquinoine ring system found in RTI 5989-240 was achieved via the Pictet-Spengler reaction. This was carried out starting with acid hydrolysis of the chiral intermediate 2.3 to give the amino acid 2.4. Bromination to remove the ortho hydrogen atoms in this compound was necessary to prevent polymerization in the Pictet-Spengler reaction which was performed using HBr and formaldehyde at 80° C. to give 2.6. This product was then protected as its tert-butoxycarbonyl ester using di-tert-butyl-di-carbonate and then debrominated catalytically using Pd/C under hydrogen at 40 psig to give the key starting material 2.8. Completion of the synthesis of RT15989-240 (14, Q=NH and $R_{18}$=$CH_3$) was accomplished by coupling 2.8 with 3-[1-(2S-amino-3-methylbutyl)-3R,4R-dimethyl-4-piperidinyl]phenol (J) using benzotriazol-1-yloxy-tris(dimethylamino)phosphonium hexafluorophosphate in THF followed by deprotection using boron tribromide in methylene chloride and silica gel chromatography.

The compounds of the present invention may be in the form of a pharmaceutically acceptable salt via protonation of the amines with a suitable acid. The acid may be an inorganic acid or an organic acid. Suitable acids include, for example, hydrochloric, hydroiodic, hydrobromic, sulfuric, phosphoric, citric, acetic, fumaric, tartaric, and formic acids.

The receptor selectivities discussed above are determined based on the binding affinities at the receptors indicated or their selectivity in opioid functional assays.

The compounds of the present invention may be used to bind opioid receptors. Such binding may be accomplished by contacting the receptor with an effective amount of the inventive compound. Of course, such contacting is preferably conducted in an aqueous medium, preferably at physiologically relevant ionic strength, pH, etc.

The inventive compounds may also be used to treat patients having disease states which are ameliorated by binding opioid receptors or in any treatment wherein temporary suppression of the kappa opioid receptor system is desired. Such diseases states include opiate addiction (such as heroin addiction), cocaine, nicotine, or ethanol addiction. The compounds of the present invention may also be used as cytostatic agents, as antimigraine agents, as immunomodulators, as immunosuppressives, as antiarthritic agents, as antiallergic agents, as virucides, to treat diarrhea, as antipsychotics, as antischizophrenics, as antidepressants, as anti-anxiety agents, anti-stress agents, as uropathic agents, as antitussives, as antiaddictive agents, as anti-smoking agents, to treat alcoholism, as hypotensive agents, to treat and/or prevent paralysis resulting from traumatic ischemia, general neuroprotection against ischemic trauma, as adjuncts to nerve growth factor treatment of hyperalgesia and nerve grafts, as anti-diuretics, as stimulants, as anti-convulsants, or to treat obesity. Additionally, the present compounds can be used in the treatment of Parkinson's disease as an adjunct to L-dopa for treatment of dyskinesia associated with the L-dopa treatment.

The compounds may be administered in an effective amount by any of the conventional techniques well-established in the medical field. For example, the compounds may be administered orally, intravenously, or intramuscularly. When so administered, the inventive compounds may be combined with any of the well-known pharmaceutical carriers
and additives that are customarily used in such pharmaceutical compositions. For a discussion of dosing forms, carriers, additives, pharmacodynamics, etc., see *Kirk-Othmer Encyclopedia of Chemical Technology*, Fourth Edition, Vol. 18, 1996, pp. 480-590, incorporated herein by reference. The patient is preferably a mammal, with human patients especially preferred. Effective amounts are readily determined by those of ordinary skill in the art. Studies by the present inventors show no toxicity and no lethality for the present compounds at amounts up to 300 mg/kg in mice.

The compounds of the present invention can be administered as a single dosage per day, or as multiple dosages per day. When administered as multiple dosages, the dosages can be equal doses or doses of varying amount, based upon the time between the doses (i.e. when there will be a longer time between doses, such as overnight while sleeping, the dose administered will be higher to allow the compound to be present in the bloodstream of the patient for the longer period of time at effective levels). Preferably, the compound and compositions containing the compound are administered as a single dose or from 2-4 equal doses per day.

Suitable compositions containing the present compounds further comprise a physiologically acceptable carrier, such as water or conventional pharmaceutical solid carriers, and if desired, one or more buffers and other excipients.

Examples

Having generally described this invention, a further understanding can be obtained by reference to certain specific examples which are provided herein for purposes of illustration only and are not intended to be limiting unless otherwise specified.
Chemistry
Synthesis of 14; Q=NH, $R_{18}$=CH$_3$.
(2S,4R)-3-Benzoyl-4-methyl-2-phenyl-1,3-oxazolidin-5-one (2.2). (R)-Alanine (8.4 g, 0.094 mol) was added into a solution of NaOH (3.78 g, 0.095 mol) in H$_2$O (94 mL), and EtOH (30 mL). The solution was heated until the solid dissolved, and then the solvent was evaporated until precipitation began. To the residue was added benzaldehyde (15 g, 0.140 mol) and 100 mL of pentane. This mixture was stirred at reflex for 8 h to remove the water by azeotropic distillation. Evaporation of the solvent gave a white solid that was dried in vacuo overnight. This solid was suspended in dichloromethane (150 mL), and a solution of benzoyl chloride (13.3 g, 0.094 mol) in dichloromethane (50 mL) was added dropwise at 0° C. After 4 h, the reaction mixture was allowed to stir at room temperature overnight. This turbid mixture was washed with H$_2$O, 5% NaHCO$_3$, 5% of NaHSO$_3$, and H$_2$O again and then dried over Na$_2$SO$_4$. Evaporation of the solvent gave a white solid. Fractional recrystallizations of this solid from CH$_2$Cl$_2$ and ether (1:2) gave 7.9 g of (2S,4R)-3-benzoyl-4-methyl-2-phenyl-1,3-oxazolidin-4-one as white crystals. [α]$^{25}_D$=−225 (c, 1.0; CHCl$_3$).

(2S,4R)-4-(4-methoxybenzyl)-4-methyl-2-phenyl-3-(phenylcarbonyl)-1,3-oxazolidin-5-one (2.3). Compound 2.2 (6.35 g, 0.023 mol) in 50 mL of THF at −78° C. was added over 20 min to a solution of LHMDS in THF (25 mL of 1 M solution in THF). After 10 min, 1.1 eq. of 4-methoxybenzyl bromide (25 mmol, 5 mL) was added in one portion. The mixture was stirred at −78° C. for 3 h and then room temperature overnight. Saturated NH$_4$Cl solution was added, the THF was removed in vacuo, 100 mL of Et$_2$O was added and the phases were separated. The organic layer was washed with 50 mL of NaHCO$_3$ solution and brine. After drying (Na$_2$SO$_4$), filtration and removal of the solvent, the residue was purified by chromatography using Si Gel ISCO column with 9% EtOAc in Hexanes as eluent. Concentration of the product fractions gave 7.4 g (82%) of 2.3 as a white solid. MP 128-129° C.; [α]$^{25}_D$=−260 (c 0.8, MeOH); $^1$H NMR δ 7.27 (1H, d, J=8 Hz), 7.19-7.14 (2H, m), 7.09-7.05 (4H, m), 6.94 (d, 2H, J=8 Hz), 6.76-6.72 (m, 4H), 5.68 (s, 1H), 3.88 (d, 1H, J=12 Hz), 3.86 (s, 3H), 3.27 (d, 1H, J=12 Hz), 2.14 (s, 3H); C NMR 175.1, 169.4, 159.6, 136.7, 131.5, 130.1, 130.0, 128.8, 128.7, 128.2, 127.2, 126.3, 114.6, 90.7, 65.9, 55.8, 40.5, 24.6; ESI MS 402 (M+1).

O,α-Dimethyl-D-tyrosine (2.4). Compound 2.3 (2.2 g, 0.0055 mol) were suspended in 20 mL of concentrated HCl solution. After nitrogen flush, the mixture was heated under reflux for 3 hours. After filtration and removal of the HCl solution, the white precipitate was dried. $^1$H NMR δ 7.24 (d, 2H, J=6 Hz), 6.91 (d, 2H, J=6 Hz), 3.77 (3H, s), 3.26 (d, 1H, J=14 Hz), 3.13 (d, 1H, J=14 Hz), 1.66 (s, 3H); C NMR 173.8, 161.3, 132.9, 115.9, 62.4, 56.4, 43.5, 23.2; ESI MS 210 (M+1). The product was used in the next step without purification.

3,5-Dibromo-O,α-dimethyl-D-tyrosine (2.5). To a solution of Compound 2.4 in distilled water (20 mL), 12 M HCl (4 mL) was added. The reaction mixture was cooled to 5° C., and bromine (2.1 mL, 41 mmol) was injected into the stirred solution. After 15 min, N$_2$ gas was passed through the reaction mixture until the product precipitated. APCI MS 366 (M+1). The crude product was used in the next step.

(3R)-6,8-Dibromo-7-methoxy-3-methyl-1,2,3,4-tetrahydroisoquinoline-3-carboxylic acid (2.6). Compound 2.5 (4.8 mmol) was added to trifluoroacetic acid (5 mL). HBr (33% in acetic acid, 0.9 mL, 4.8 mmol) was added dropwise to the reaction mixture under nitrogen atmosphere. Upon the addition of the acid, formaldehyde (8.64 mmol, 260 mg, 0.7 mL) was added dropwise and the mixture stirred at 70-80° C. for 17 h. The reaction mixture was cooled, dried and concentrated. APCI MS 378 (M+1). The product was used in the next step.

(3R)-6,8-Dibromo-2-(tert-butoxycarbonyl)-7-methoxy-3-methyl-1,2,3,4-tetrahydroisoquinoline-3-carboxylic acid (2.7). Compound 2.6 (4.8 mmol) was dissolved in DMF (7 mL) and water (2 mL). Triethylamine (1.01 g, 0.01 mol) was added, followed by di-tert-butyl di-carbonate (1.57 g, 0.007 mmol). The reaction mixture was stirred at RT for 4 h and then concentrated to dryness. The resulting residue was treated with water (30 mL) and EtOAc (30 mL), KHSO$_4$ (2 g) was added to the mixture (pH=2), the organic layer was separated, dried, and concentrated. The product was purified by chromatography using Si Gel ISCO column, using 35% EtOAc in Hexanes as eluent to afford 500 mg of 2.7 as a syrup. $^1$H NMR δ 7.55 (s, 1H), 4.84 (d, 1H, J=16 Hz), 4.54 (d, 1H, J=16 Hz), 3.85 (s, 3H), 3.19 (d, 1H, J=16 Hz), 2.92 (d, 1H, J=16 Hz), 1.47 (s, 9H), 1.42 (s, 3H); C NMR 177.7, 154.7, 138.1, 135.4, 132.9, 118.6, 117.9, 62.5, 62.0, 46.1, 41.7, 29.1, 28.3, 23.9; ESI MS 478 (M+1).

(3R)-2-(tert-Butoxycarbonyl)-7-methoxy-3-methyl-1,2,3,4-tetrahydroisoquinoline-3-carboxylic acid (2.8). Triethylamine (303 mg, 3 mmol) and 10% Pd—C (20 mg) were added to Compound 2.7 (500 mg, 1.05 mmol) in MeOH (5 mL) and the mixture was hydrogenated on a Parr shaker at 40 PSI for 90 min. The mixture was filtered through Celite and concentrated. The product was used in the next step.

tert-Butyl (3R)-3-{[(1S)-1-{[(3R,4R)-4-(3-hydroxyphenyl)-3,4-dimethylpiperidin-1-yl]methyl}-2-methylpropyl]carbamoyl}-7-methoxy-3-methyl-3,4-dihydroisoquinoline-2(1H)-carboxylate (2.9). Compound 2.8 (200 mg, 0.623 mmol), 3-{(3R,4R)-1-[(2S)-2-amino-3-methylbutyl]-3,4-dimethylpiperidin-4-yl}phenol (J) (181 mg, 0.623 mmol) and BOP reagent (275 mg, 0.623 mmol) were dissolved in THF (20 mL). Triethylamine (1 mL) was added and the solution was stirred at room temperature for 3 h. The solution was extracted with $CH_2Cl_2$ and saturated $NaHCO_3$ solution. The organic layer was dried and purified by column chromatography to afford 250 mg, (68%) of 2.9.

(3R)-7-Hydroxy-N-[(1S)-1-{[(3R,4R)-4-(3-hydroxyphenyl)-3,4-dimethylpiperidin-1-yl]methyl}-2-methylpropyl]-3-methyl-1,2,3,4-tetrahydroisoquinoline-3-carboxamide (RTI-5989-240) (14, Q=NH, $R_{18}$=$CH_3$). Compound 2.9 (25 mg, 0.05 mmol) was dissolved in 10 mL of DCM, and $BBr_3$ (0.5 mL of 1M DCM solution) was added dropwise at −78° C. After 3 h, the reaction mixture was washed with saturated $NaHCO_3$ and DCM. The organic layer was dried and purified by chromatography using a Si Gel ISCO column to afford 21 mg (88%) of 14 (Q=NH, $R_{18}$=$CH_3$). $^1$H NMR δ 6.86 (1H, t, J=8 Hz), 6.66 (1H, d, J=8 Hz), 6.51-6.46 (2H, m), 6.35-6.31 (2H, m), 6.25 (1H, d, J=2 Hz), 3.78 (1H, d, J=11 Hz), 3.65 (2H, m), 2.94 (1H, d, J=11 Hz), 2.44-2.10 (6H, m), 1.95 (1H, m), 1.64 (2H, m), 1.24 (1H, d, J=7.2 Hz), 1.11 (3H, s), 1.04 (3H, s), 0.97-0.92 (6H, m), 0.35 (3H, d, J=7 Hz); C NMR 178.0, 158.3, 157.1, 153.5, 137.4, 131.1, 130.4, 126.1, 118.5, 115.1, 114.2, 113.6, 113.5, 62.2, 57.3, 52.9, 47.9, 46.1, 40.6, 37.4, 32.5, 28.4, 27.9, 20.3, 18.0, 17.0, 10.6. Elemental analysis, Calcd for $C_{29}H_{41}Cl_2N_3O_3 \cdot 2.5H_2O$. C, 58.28; H, 8.10; N, 7.03. Found: C, 58.47; H, 7.85; N, 7.06.

Biological
In Vitro

Measures of opioid receptor antagonism and specificity were obtained by monitoring the ability of selected test compounds to inhibit stimulation of [$^{35}$S]GTPγS binding produced by the selective agonists (D-Ala$^2$, MePhe$^4$, Gly-ol$^5$) enkephalin (DAMGO, mu receptor), cyclo[D-Pen$^2$, D-Pen$^5$] enkephalin (DPDPE, delta) and 5,7,8-(−)-N-methyl-N-[7-(1-pyrrolidinyl)-1-oxaspiro[4,5]dec-8-yl]benzeneacetamide (U69,593, kappa) in cloned human receptors, Table 1.

TABLE 1

Inhibition of Agonist Stimulated [$^{35}$S]GTPγS Binding by Compounds in Cloned Human μ, δ, and κ Opioid Receptors

| RTI-5989- | μ, DAMGO $K_e$ (nM) | δ, DPDPE $K_e$ (nM) | κ, U69,593 $K_e$ (nM) | μ/κ | δ/κ |
|---|---|---|---|---|---|
| 239 | 3.8 | 36.8 | 0.93 | 4 | 40 |
| 240$^+$ | 3.6 | 840 | 0.03 | 120 | 28,000 |

$^+$RTI-5989-240 = 14;
Q = NH,
$R_{18}$ = $CH_3$.

Results and Discussion

Compounds RTI-5989-239 and RTI-5989-240 show high potency for the kappa opioid receptor in the [$^{35}$S]GTPγS in vitro functional assay. Note that RTI-5989-240 with a $K_e$ value of 0.03 has subnanomolar potency, and since its $K_e$ values at the μ and δ opioid receptors are 3.6 and 840 nM, it is highly selective for the kappa opioid receptor.

CONCLUSIONS

The compounds of the present invention are potent kappa opioid receptor antagonists in an in vitro functional test. They show good selectivity relative to the mu and delta opioid receptors.

REFERENCES (1) Aldrich, J. V. Analgesics. In *Burger's Medicinal Chemistry and Drug Discovery*, Wolff, M. E. Eds.; John Wiley & Sons: New York, 1996; Vol. 3.
(2) Volpicelli, J. R.; Alterman, A. I.; Hayashida, M.; O'Brien, C. P. Naltrexone in the treatment of alcohol dependence. *Arch. Gen. Psychiatry* 1992, 49, 876-879.
(3) Volpicelli, J. R.; Watson, N. T.; King, A. C.; Sherman, C. E.; O'Brien, C. P. Effect of naltrexone on alcohol "high" in alcoholics. *Am. J Psychiatry* 1995, 152, 613-615.
(4) Marki, A.; Monory, K.; Otvos, F.; Toth, G.; Krassnig, R.; Schmidhammer, H.; Traynor, J. R.; Roques, B. P.; Maldonado, R.; Borsodi, A. Mu-opioid receptor specific antagonist cyprodime: characterization by in vitro radioligand and [35S]GTPgammaS binding assays. *Eur J Pharmacol* 1999, 383(2), 209-14.
(5) Portoghese, P. S. The design of -selective opioid receptor antagonists. *Il Fannaco* 1993, 48(2), 243-251.
(6) Portoghese, P. S.; Lipkowski, A. W.; Takemori, A. E. Binaltorphimine and nor-binaltorphimine, potent and selective-opioid receptor antagonists. *Life Sci.* 1987, 40(13), 1287-1292.
(7) Olmsted, S. L.; Takemori, A. E.; Portoghese, P. S. A remarkable change of opioid receptor selectivity on the attachment of a peptidomimetic address element to the antagonist, natrindole: 5'-[N$^2$-alkylamidino)methyl]naltrindole derivatives as a novel class of opioid receptor antagonists. *J. Med. Chem.* 1993, 36(1), 179-180.
(8) Jones, R. M.; Hjorth, S. A.; Schwartz, T. W.; Portoghese, P. S. Mutational evidence for a common kappa antagonist binding pocket in the wild-type kappa and mutant mu[K303E] opioid receptors. *J Med Chem* 1998, 41(25), 4911-4.
(9) Schwyzer, R. ACTH: A short introductory review. *Ann. N.Y. Acad. Sci.* 1977, 247, 3-26.
(10) Trujillo, K. A.; Akil, H. Changes in prodynorphin peptide content following treatment with morphine or amphetamine: possible role in mechanisms of action of drug of abuse. *NIDA Res Monogr* 1989, 95, 550-1.
(11) Smiley, P. L.; Johnson, M.; Bush, L.; Gibb, J. W.; Hanson, G. R. Effects of cocaine on extrapyramidal and limbic dynorphin systems. *J Pharmacol Exp Ther* 1990, 253(3), 938-43. (12) Corbett, A. D.; Paterson, S. J.; McKnight, A. T.; Magnan, J.; Kosterlitz, H. W. Dynorphin and dynorphin are ligands for the kappa-subtype of opiate receptor. *Nature* 1982, 299(5878), 79-81.
(13) Spanagel, R.; Herz, A.; Shippinberg, T. A. Opposing tonically active endogenous opioid systems modulate the mesolimbic dopaniinergic pathway. *Proc. Natl. Acad. Sci. U.S.A.* 1992, 89, 2046-2050.

(14) Spanagel, R.; Shippenberg, T. S. Modulation of morphine-induced sensitization by endogenous opioid systems in the rat. *Neurosci. Lett.* 1993, 153, 232-236.
(15) Zadina, J. E.; Hackler, L.; Ge, L.-J.; Kastin, A. J. A potent and selective endogenous agonist for the -opiate receptor. *Nature* 1997, 386, 499-502.
(16) Zimmerman, D. M.; Nickander, R.; Homg, J. S.; Wong, D. T. New structural concepts for narcotic antagonists defined in a 4-phenylpiperidine series. *Nature* 1978, 275, 332-334.
(17) Zimmerman, D. M.; Smits, S.; Nickander, R. Further investigation of novel 3-methyl-4-phenylpiperidine narcotic antagonists. In *Proceedings of the 40th Annual Scientific Meeting of the Committee on Problems of Drug Dependence,* 1978, pp. 237-247.
(18) Zimmerman, D. M.; Smits, S. E.; Hynes, M. D.; Cantrell, B. E.; Reamer, M.; Nickander Structural requirements for affinity and intrinsic activity at the opiate receptor defined in 4-phenylpiperidine and related series. In *Problems of Drug Dependence* 1981, *Proceedings of the 43rd Annual Scientific Meeting of the Committee on Problems of Drug Dependence, Inc.,* Harris, L. S. Eds.; 1981, pp. 112-116.
(19) Zimmerman, D. M.; Smits, S. E.; Hynes, M. D.; Cantrell, B. E.; Reamer, M.; Nickander, R. Structural requirements for affinity and intrinsic activity at the opiate receptor defined in 4-phenylpiperidine and related series. In *Problems of Drug Dependence,* 1981, *Proceedings of the 43rd Annual Scientific Meeting,* The committee on Problems of Drug Dependence, Inc., Harris, L. S. Eds.; Committee on Problems of Drug Dependence, Inc.: 1982; Vol. NIDA Research Monograph 41, pp. 112-118.
(20) Zimmerman, D. M.; Cantrell, B. E.; Swartzendruber, J. K.; Jones, N. D.; Mendelsohn, L. G.; Leander, J. D.; Nickander, R. C. Synthesis and analgesic properties of N-substituted trans-4a-aryldecahydroisoquinolines. *J. Med. Chem.* 1988, 31, 555-560.
(21) Zimmerman, D. M.; Leander, J. D.; Cantrell, B. E.; Reel, J. K.; Snoddy, J.; Mendelsohn, L. G.; Johnson, B. G.; Mitch, C. H. Structure-activity relationships of the trans-3,4-dimethyl-4-(3-hydroxyphenyl)piperidine antagonists for and opioid receptors. *J. Med. Chem.* 1993, 36(20), 2833-2841.
(22) Zimmerman, D. M.; Hermann, R. B.; Mitch, C. H.; Shaw, W. N.; Mendelsohn, L. G.; Leander, J. D. Opioid receptor antagonists: Comparison of trans-3,4-dimethyl-4-phenylpiperidines and their use in the development of a model of opioid receptors. *Pharmacol. Rev.* in press.
(23) Thomas, J. B.; Mascarella, S. W.; Rothman, R. B.; Partilla, J. S.; Xu, H.; McCullough, K. B.; Dersch, C. M.; Cantrell, B. E.; Zimmerman, D. M.; Carroll, F. I. Investigation of the N-substituent conformation governing potency and receptor subtype-selectivity in (+)-(3R,4R)-dimethyl-4-(3-hydroxyphenyl)piperidine opioid antagonists. *J. Med. Chem.* 1998, 41(11), 1980-1990.
(24) Thomas, J. B.; Fall, M. J.; Cooper, J. B.; Rothman, R. B.; Mascarella, S. W.; Xu, H.; Partilla, J. S.; Dersch, C. M.; McCullough, K. B.; Cantrell, B. E.; Zimmerman, D. M.; Carroll, F. I. Identification of opioid receptor subtype-selective N-substituent for (+)-(3R,4R)-dimethyl-4-(3-hydroxyphenyl)piperidine. *J. Med. Chem.* 1998, 41(26), 5188-5197.
(25) Werner, J. A.; Cerbone, L. R.; Frank, S. A.; Ward, J. A.; Labib, P.; Tharp-Taylor, R. W.; Ryan, C. W. Synthesis of trans-3,4-dimethyl-4-(3-hydroxyphenyl)piperidine opioid antagonists: Application of the cis-thermal elimination of carbonates to alkaloid synthesis. *J. Org. Chem.* 1996, 61, 587-597.
(25) U.S. Patent Publication No. 2002/0132828 and U.S. Pat. No. 6,974,824.
(26) U.S. Patent Publication No. 2006/0183743

Obviously, numerous modifications and variations of the present invention are possible in light of the above teachings. It is therefore to be understood that within the scope of the appended claims, the invention may be practiced otherwise than as specifically described herein.

The invention claimed is:
1. A kappa opioid receptor antagonist compound represented by the formula (I):

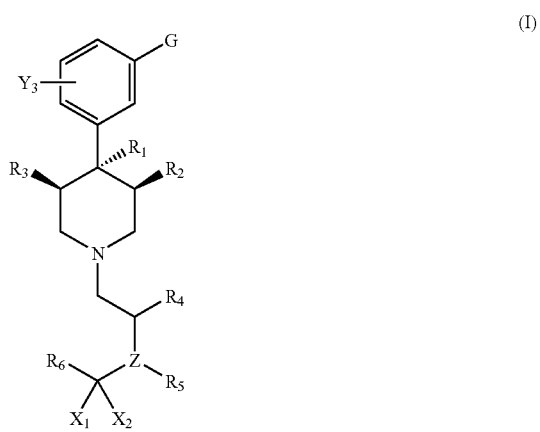

wherein
G is H, OH, $OC_{1-6}$ alkyl, $OCOC_{1-8}$ alkyl, $CONH_2$, NHCHO, $NH_2$, $NHSO_2C_{1-8}$ alkyl, or $NHCO_2C_{1-8}$ alkyl;
$R_1$ is $C_{1-8}$ alkyl, or one of the following structures:

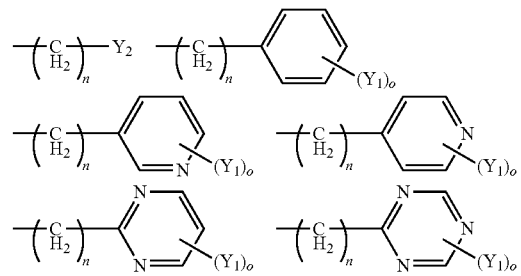

each $Y_1$ is, independently, H, Br, Cl, F, CN, $CF_3$, $NO_2$, $N_3$, $OR_8$, $CO_2R_9$, $C_{1-6}$ alkyl, $NR_{10}R_{11}$, $NHCOR_{12}$, $NHCO_2R_{12}$, $CONR_{13}R_{14}$, or $CH_2(CH_2)_nY_2$,
or two adjacent $Y_1$ groups form a —O—$CH_2$—O— or —O—$CH_2CH_2$—O— group;
each $Y_2$ is, independently, H, $CF_3$, $CO_2R_9$, $C_{1-6}$alkyl, $NR_{10}R_{11}$, $NHCOR_{12}$, $NHCO_2R_{12}$, $CONR_{13}R_{14}$, $CH_2OH$, $CH_2OR_8$, or $COCH_2R_9$;
$Y_3$ is H, Br, Cl, F, CN, $CF_3$, $NO_2$, $N_3$, $OR_8$, $CO_2R_9$, $C_{1-6}$ alkyl, $NR_{10}R_{11}$, $NHCOR_{12}$, $NHCO_2R_{12}$, $CONR_{13}R_{14}$, or $CH_2(CH_2)_nY_2$;
$R_2$ is H, $C_{1-8}$ alkyl, $C_{3-8}$ alkenyl, $C_{3-8}$ alkynyl or $CH_2$-aryl substituted by one or more groups $Y_1$;
$R_3$ is H, $C_{1-8}$ alkyl, $C_{3-8}$ alkenyl, $C_{3-8}$ alkynyl or $CH_2$-aryl substituted by one or more groups $Y_1$;
wherein $R_2$ and $R_3$ may be bonded together to form a $C_{2-8}$ alkyl group;

$R_4$ is hydrogen, $C_{1-8}$ alkyl, $CO_2C_{1-8}$ alkylaryl substituted by one or more groups $Y_1$, $CH_2$-aryl substituted by one or more groups $Y_1$ or $CO_2C_{1-8}$ alkyl;

Z is N, O or S, wherein when Z is O or S, there is no $R_5$;

$R_5$ is H, $C_{1-8}$ alkyl, $C_{3-8}$ alkenyl, $C_{3-8}$ alkynyl, $CH_2CO_2C_{1-8}$ alkyl, $CO_2C_{1-8}$ alkyl or $CH_2$-aryl substituted by one or more groups $Y_1$;

n is 0, 1, 2 or 3;

o is 0, 1, 2, or 3;

$R_6$ is a group selected from the group consisting of structures (a)-(p):

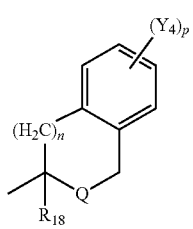
(a)

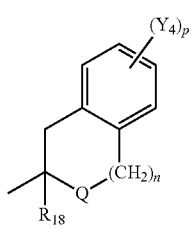
(b)

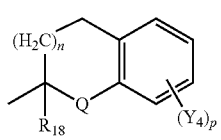
(c)

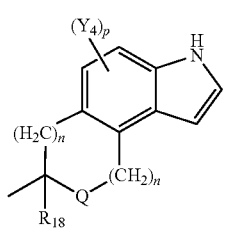
(d)

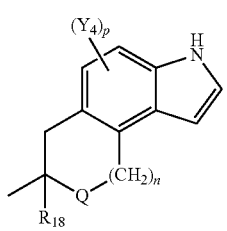
(e)

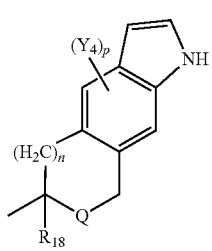
(f)

-continued

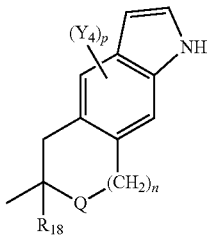
(g)

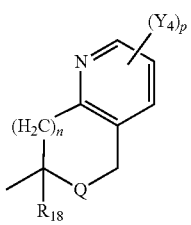
(h)

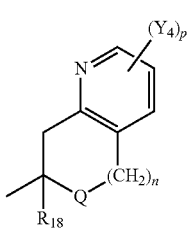
(i)

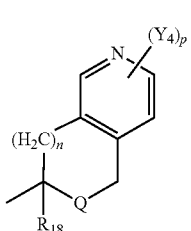
(j)

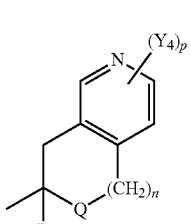
(k)

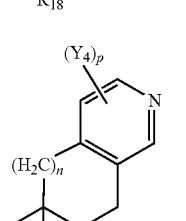
(l)

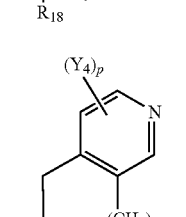
(m)

(n)

(o)

(p)

Q is $NR_7$, $CH_2$, O, S, SO, or $SO_2$;
each $Y_4$ is, independently, H, Br, Cl, F, CN, $CF_3$, $NO_2$, $N_3$, $OR_8$, $CO_2R_9$, $C_{1-6}$ alkyl, $NR_{10}R_{11}$, $NHCOR_{12}$, $NHCO_2R_{12}$, $CONR_{13}R_{14}$, or $CH_2(CH_2)_nY_2$,
or two adjacent $Y_4$ groups form a —O—$CH_2$—O— or —O—$CH_2CH_2$—O— group;
p is 0, 1, 2, or 3;
$Y_5$ is H, Br, Cl, F, CN, $CF_3$, $NO_2$, $N_3$, $OR_8$, $CO_2R_9$, $C_{1-6}$ alkyl, $NR_{10}R_{11}$, $NHCOR_{12}$, $NHCO_2R_{12}$, $CONR_{13}R_{14}$, or $CH_2(CH_2)_nY_2$;
$X_1$ is hydrogen, $C_{1-8}$ alkyl, $C_{3-8}$alkenyl, or $C_{3-8}$alkynyl;
$X_2$ is hydrogen, $C_{1-8}$alkyl, $C_{3-8}$alkenyl, or $C_{3-8}$alkynyl;
or $X_1$ and $X_2$ together form =O, =S, or =NH;
$R_7$ is H, $C_{1-8}$ alkyl, $CH_2$-aryl substituted by one or more substituents $Y_1$, $NR_{10}R_{11}$, $NHCOR_{12}$, $NHCO_2R_{13}$, $CONR_{14}R_{15}$, $CH_2(CH_2)_nY_2$, or C(=NH)$NR_{16}R_{17}$;
each of $R_8$, $R_9$, $R_{10}$, $R_{11}$, $R_{12}$, $R_{13}$, $R_{14}$, $R_{15}$, $R_{16}$ and $R_{17}$ is, independently, H, $C_{1-8}$ alkyl, $CH_2$-aryl substituted by one or more substituents H, OH, Br, Cl, F, CN, $CF_3$, $NO_2$, $N_3$, $C_{1-6}$ alkyl, or $CH_2(CH_2)_nY_2'$;
$Y_2'$ is H, $CF_3$, or $C_{1-6}$ alkyl;
$R_{18}$ is $C_{1-8}$ alkyl, $C_{2-8}$ alkenyl, $C_{3-8}$ alkenyl, $CH_2OR_5$, or $CH_2$-aryl substituted by one or more substituents $Y_1$;
or a pharmaceutically acceptable salt thereof.

2. The kappa opioid receptor antagonist of claim 1, wherein $Y_3$ is H.

3. The kappa opioid receptor antagonist of claim 1, wherein $R_1$ is $C_{1-8}$ alkyl, or one of the following structures:

$Y_3$ is H;
$R_2$ and $R_3$ are each, independently, H or $C_{1-8}$ alkyl, wherein $R_2$ and $R_3$ cannot both be H at the same time; and
$R_7$ is H, $C_{1-8}$ alkyl, $CH_2$-aryl substituted by one or more substituents $Y_1$, $NR_{10}R_{11}$, $NHCOR_{12}$, $NHCO_2R_{13}$, $CONR_{14}R_{15}$, or $CH_2(CH_2)_nY_2$.

4. The kappa opioid receptor antagonist of claim 1, wherein
$R_1$ is $C_{1-8}$ alkyl;
$Y_2$ is H, $CF_3$, $CO_2R_9$, $C_{1-6}$ alkyl, $NR_{10}R_{11}$, $NHCOR_{12}$, $NHCO_2R_{12}$, $CONR_{13}R_{14}$, $CH_2OH$, $CH_2OR_8$, or $COCH_2R_9$;
$Y_3$ is H;
$R_2$ and $R_3$ are each, independently, H or methyl, wherein $R_2$ and $R_3$ cannot both be H at the same time;
$R_4$ is H, $C_{1-8}$ alkyl, $CO_2C_{1-8}$alkyl, or $CH_2$-aryl substituted by one or more substituents $Y_1$ and the stereocenter adjacent to $R_4$ is in an (S) configuration;
$R_5$ is H, $C_{1-8}$ alkyl, or $CH_2CO_2C_{1-8}$ alkyl;
$R_6$ is a group having a formula selected from the group consisting of structures (a)-(c) and (h)-(p); and
$R_7$ is H, $C_{1-8}$alkyl, $CH_2$-aryl substituted by one or more substituents $Y_1$, $NR_{10}R_{11}$, $NHCOR_{12}$, $NHCO_2R_{13}$, $CONR_{14}R_{15}$, or $CH_2(CH_2)_nY_2$.

5. The kappa opioid receptor antagonist of claim 1, wherein
$R_1$ is methyl,
$Y_2$ is H, $CF_3$, $CO_2R_9$, $C_{1-6}$ alkyl, $NR_{10}R_{11}$, $NHCO_2R_{12}$, $NHCO_2R_{12}$, $CONR_{13}R_{14}$, $CH_2OH$, $CH_2OR_8$, or $COCH_2R_9$;
$Y_3$ is H;
$R_2$ and $R_3$ are each H or methyl, such that when $R_2$ is H, $R_3$ is methyl and vice versa;
$R_4$ is $C_{1-8}$ alkyl, or $CO_2C_{1-8}$ alkyl, and the stereocenter adjacent to $R_4$ has a configuration of (S);
$R_5$ is H;
$R_6$ is a group having a formula selected from the group consisting of structures (a) and (b); and
$R_7$ is H, $C_{1-8}$ alkyl, $CH_2$-aryl substituted by one or more substituents $Y_1$ or $CH_2(CH_2)_nY_2$.

6. The kappa opioid receptor antagonist of claim 1, which is represented by formula 14, 15, 16, 17 or 18:

14

15

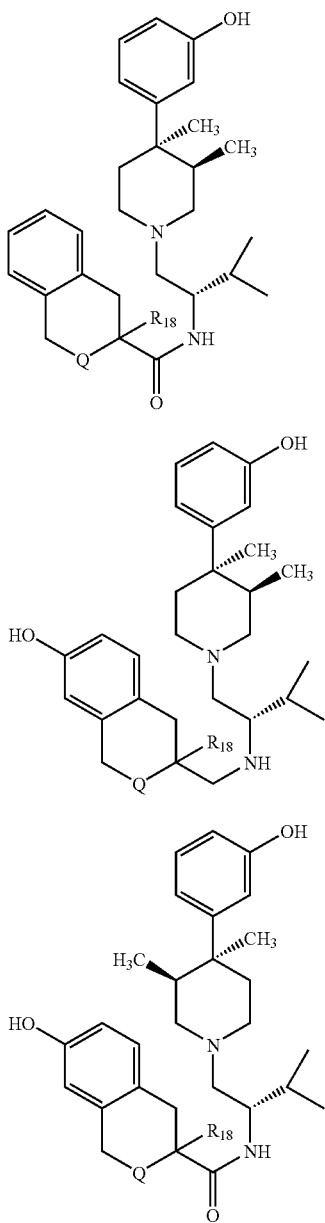

wherein Q and R$^{18}$ are as defined in claim 1.

7. The kappa opioid receptor antagonist of claim 1, wherein Q is NH and R$^{18}$ is C$_{1-8}$ alkyl.

8. The kappa opioid receptor antagonist of claim 1, wherein Q is NH and R$^{18}$ is C$_{2-8}$ alkenyl.

9. The kappa opioid receptor antagonist of claim 1, wherein Q is NH and R$^{18}$ is C$_{3-8}$ alkenyl.

10. The kappa opioid receptor antagonist of claim 1, wherein Q is NH and R$^{18}$ is CH$_2$-aryl substituted by one or more groups Y$_1$.

11. The kappa opioid receptor antagonist of claim 1, wherein Q is NH and R$^{18}$ is C$_{1-4}$ alkyl.

12. The kappa opioid receptor antagonist of claim 1, wherein Q is NH and R$^{18}$ is methyl.

13. The kappa opioid receptor antagonist of claim 6, wherein Q is NH and R$^{18}$ is C$_{1-8}$ alkyl.

14. The kappa opioid receptor antagonist of claim 6, wherein Q is NH and R$^{18}$ is C$_{2-8}$ alkenyl.

15. The kappa opioid receptor antagonist of claim 6, wherein Q is NH and R$^{18}$ is C$_{3-8}$ alkenyl.

16. The kappa opioid receptor antagonist of claim 6, wherein Q is NH and R$^{18}$ is CH$_2$-aryl substituted by one or more groups Y$_1$.

17. The kappa opioid receptor antagonist of claim 6, wherein Q is NH.

18. The kappa opioid receptor antagonist of claim 6, wherein Q is NH and R$^{18}$ is C$_{1-4}$ alkyl.

19. The kappa opioid receptor antagonist of claim 6, wherein Q is NH and R$^{18}$ is methyl.

20. The kappa opioid receptor antagonist of claim 1, which has a κ/μ selectivity of at least 2:1.

21. The kappa opioid receptor antagonist of claim 1, which has a κ/μ selectivity of at least 50:1.

22. The kappa opioid receptor antagonist of claim 1, which has a κ/μ selectivity of at least 100:1.

23. The kappa opioid receptor antagonist of claim 1, which has a κ/δ selectivity of at least 2:1.

24. The kappa opioid receptor antagonist of claim 1, which has a κ/δ selectivity of at least 20:1.

25. The kappa opioid receptor antagonist of claim 1, which has a κ/δ selectivity of at least 250:1.

26. The kappa opioid receptor antagonist of claim 1, which has a κ/μ selectivity of at least 100:1 and which has a κ/δ selectivity of at least 200:1.

27. A pharmaceutical composition comprising an effective amount of the kappa opioid receptor antagonist of claim 1 and a physiologically acceptable carrier.

28. The pharmaceutical composition of claim 27, which is an injectable composition.

29. The pharmaceutical composition of claim 27, which is an orally administrable composition.

30. The pharmaceutical composition of claim 27, which is an orally administrable composition in a form selected from the group consisting of tablets, capsules, troches, powders, solutions, dispersions, emulsions and suspensions.

31. A method of making the pharmaceutical composition of claim 27, comprising combining the kappa opioid receptor antagonist and the physiologically acceptable carrier.

32. A method of binding a kappa opioid receptor in a subject in need thereof, comprising administering to the subject an effective amount of the kappa opioid receptor antagonist of claim 1.

* * * * *

UNITED STATES PATENT AND TRADEMARK OFFICE
CERTIFICATE OF CORRECTION

PATENT NO. : 8,048,895 B2  Page 1 of 1
APPLICATION NO. : 12/105814
DATED : November 1, 2011
INVENTOR(S) : Frank Ivy Carroll et al.

It is certified that error appears in the above-identified patent and that said Letters Patent is hereby corrected as shown below:

In column 11, line 43
"$C_{29}H_{41}Cl_2N_3O_3.2.5H_2O.$" should read --$C_{29}H_{41}Cl_2N_3O_3 \cdot 2.5H_2O$.--.

Signed and Sealed this
Third Day of April, 2012

David J. Kappos
*Director of the United States Patent and Trademark Office*